(12) United States Patent
Hall

(10) Patent No.: US 6,348,174 B1
(45) Date of Patent: Feb. 19, 2002

(54) BIOHAZARDOUS WASTE SOURCE STERILIZER SYSTEM AND PROCESSING METHOD

(75) Inventor: John L. Hall, Tracy, CA (US)

(73) Assignee: Darlene Hall, Edmonds, WA (US)

( * ) Notice: Subject to any disclaimer, the term of this patent is extended or adjusted under 35 U.S.C. 154(b) by 0 days.

(21) Appl. No.: 09/455,418

(22) Filed: Dec. 6, 1999

(51) Int. Cl.7 .............. A61L 2/08; F26B 19/00; B08B 5/00; B08B 9/00
(52) U.S. Cl. .......... 422/26; 422/295; 422/307; 34/236; 134/31; 134/11; 134/22.15; 134/42
(58) Field of Search .................. 422/1, 26, 28, 422/32, 33, 120, 291–299, 300–309; 134/31, 11, 42, 22.15, 61; 68/210; 34/236

(56) References Cited

U.S. PATENT DOCUMENTS

| | | | |
|---|---|---|---|
| 5,084,250 A | 1/1992 | Hall | 422/292 |
| 5,294,412 A | 3/1994 | Orlando | 422/295 |
| 5,389,347 A | 2/1995 | Hall | 422/307 |
| 5,470,546 A | 11/1995 | Hall | 422/292 |
| 5,614,157 A | 3/1997 | Hall | 422/307 |
| 5,746,988 A | 5/1998 | Hall | 422/292 |

Primary Examiner—Robert J. Warden, Sr.
Assistant Examiner—Monzer R. Chorbaji
(74) Attorney, Agent, or Firm—Harris Zimmerman, Esq.

(57) ABSTRACT

Infectious wastes originating in hospitals or other locations are deposited into a sealable, pressure resistant, portable sterilizer vessel at the source of the wastes. The sterilizer vessel rides on wheels enabling travel of the filled vessel to a sterilization station at another location where steam is directed into the vessel to perform the sterilization. Operators need not transfer unprocessed infectious waste from a collection cart to a fixed sterilization vessel at the sterilization site. In the preferred form, handler exposure to unprocessed wastes is further reduced by creating an airflow from the vessel opening to a filter while the vessel is opened for deposit of wastes.

22 Claims, 9 Drawing Sheets

BIOHAZARDOUS WASTE SOURCE STERILIZER SYSTEM AND PROCESSING METHOD

TECHNICAL FIELD

This invention relates to the processing of infectious wastes at medical facilities or other locations and more particularly to apparatus and methods for collecting and sterilizing such wastes.

BACKGROUND OF THE INVENTION

Potentially infectious wastes which originate in hospitals, medical clinics or other locations must be sterilized prior to being disposed of at landfills or other garbage disposal sites. Such wastes may be of various types of which used bandages, specimen containers and used hypodermic needles are examples.

In the typical practice medical personnel or others deposit such wastes in temporary containers which are situated in the hospital or the like at the locations where the wastes originate. The containers are lined with disposable plastic bags. The filled bags of unprocessed waste are transferred to a wheeled collection cart which is traveled to a sterilization station that is usually located some distance away from the locations at which the wastes originate. The bags are then transferred to a sealable pressure resistant sterilizer vessel which is a built in component of the sterilization station. Sterilization is typically effected by directing high temperature steam into the sealed sterilizer vessel for a period of time sufficient to destroy infectious organisms in the waste.

Collection of the bags of unprocessed waste at the source and subsequent transfer of the bags from the collection cart to the sterilizer can cause spatter and air flow towards the persons who perform the operations. This has necessitated sanitation procedures which complicate the processing of the wastes and add significantly to operating costs. It would be advantageous if this repeated handling of unsterilized wastes were minimized or eliminated.

The present invention is directed to overcoming one or more of the problems discussed above.

SUMMARY OF THE INVENTION

In one aspect, this invention provides biohazardous waste processing apparatus having a waste sterilizer vessel forming a chamber with an opening for receiving the wastes. The opening is sealable by a sealing closure to enable sterilization of the contents of the vessel by admission of steam into the chamber. The sterilizer vessel is also a portable waste collection cart which rides on support wheels enabling travel of the sterilizer vessel between a first location at which the waste is collected and a second location at which sterilization is performed.

In another aspect of the invention, biohazardous waste collection and processing apparatus includes a portable sealable waste collection vessel formed of pressure resistant and thermally insulative material and having an opening through which biohazardous waste is deposited in the vessel. The waste collection vessel is supported on wheels which enable travel of the vessel between a first location at which the waste originates and a second location at which the wastes within the vessel are sterilized by direction of steam into the vessel. The apparatus further includes an openable lid for closing the opening at the first location, the lid being temporarily replaceable by a sealing closure at the second location. The sealing closure seals the vessel at the second location during direction of steam into the vessel.

In still another aspect, the invention provides a method for processing biohazardous wastes which originate at a first location and which are sterilized at a second location. Steps in the method include utilizing a wheeled sealable pressure resistant sterilizer vessel at the first location for receiving said wastes thereat, wheeling the vessel to the second location, temporarily sealing the vessel at the second location while the wastes remain therein, and sterilizing the wastes at the second location by injecting steam into the vessel prior to removal of the wastes from the vessel.

The invention reduces exposure of handlers to infectious wastes by utilizing a portable sterilizer chamber as a waste receiving or collection cart at the source of the wastes. The cart may then be wheeled to another location where the sterilization is performed without requiring any transfer of the wastes from the cart to a sterilizer. Optionally, the still unemptied cart may be used to transport the now sterilized waste to still another location where the waste is dumped into a compactor and transferred to a transportable processed waste receiving bin. This enables the waste processing system as a whole to be compact and flexible with regard to the location of system components. In the preferred form of the invention, medical staff or others who first deposit infectious wastes in the portable sterilizer chamber are protected by creating an air flow from the chamber opening to a filter at times when the chamber lid is open.

The invention, together with further aspects and advantages thereof, may be further understood by reference to the following description of the preferred embodiment and by reference to the accompanying drawings.

DETAILED DESCRIPTION OF THE PREFERRED EMBODIMENTS

Figure 1:
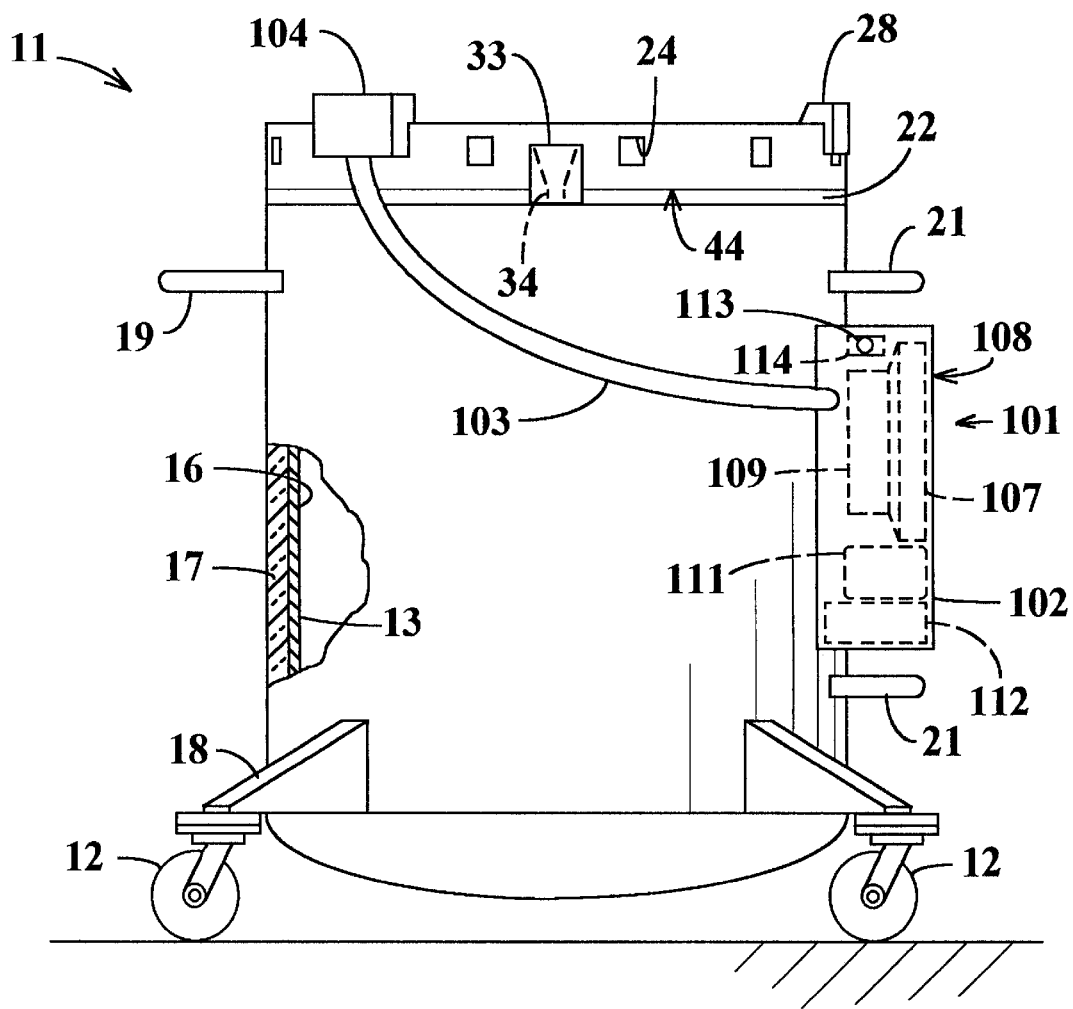
FIG. 1 is a side view of a combined sterilizer and waste collection cart embodying the invention.
Figure 2:
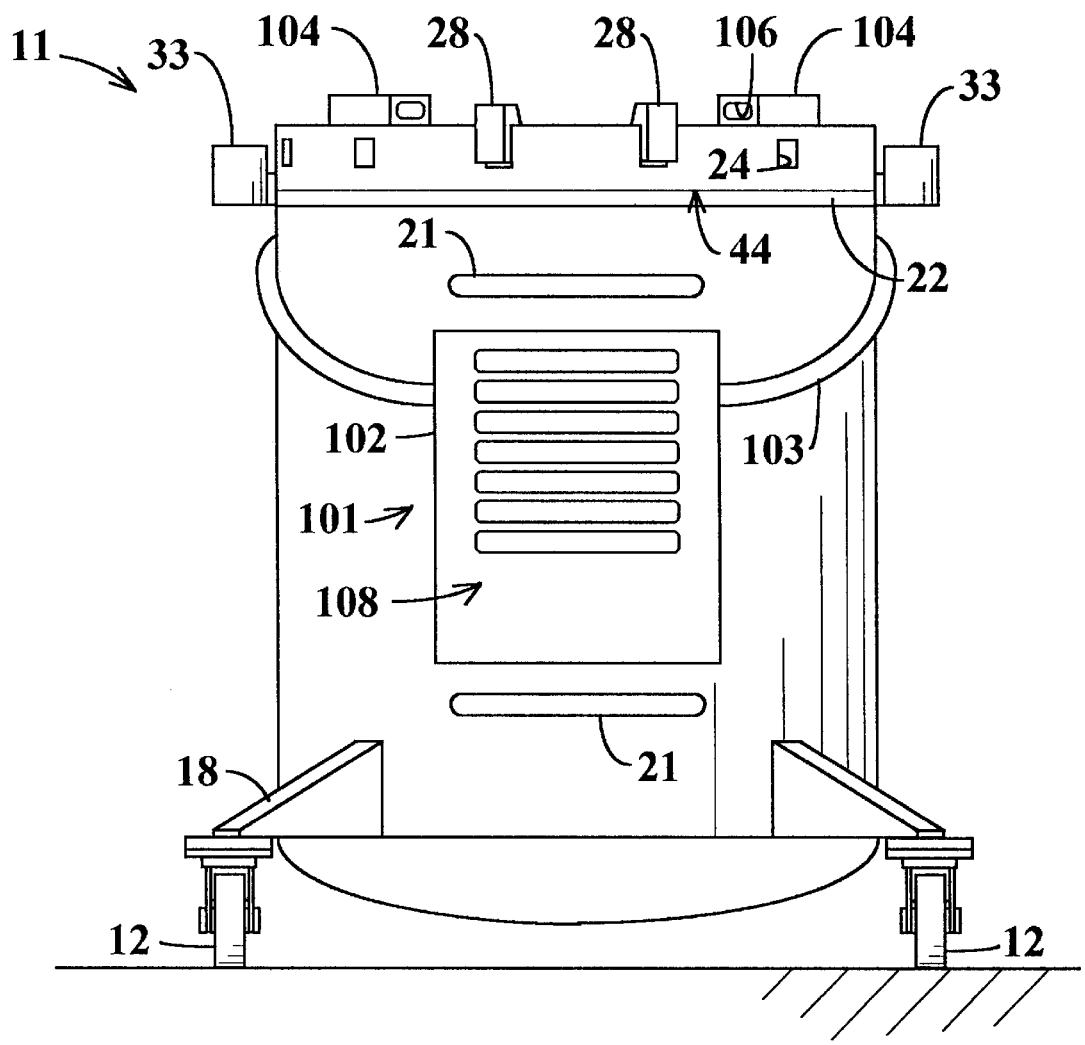
FIG. 2 is a frontal view of the sterilizer and waste collection cart of FIG. 1
Figure 3:
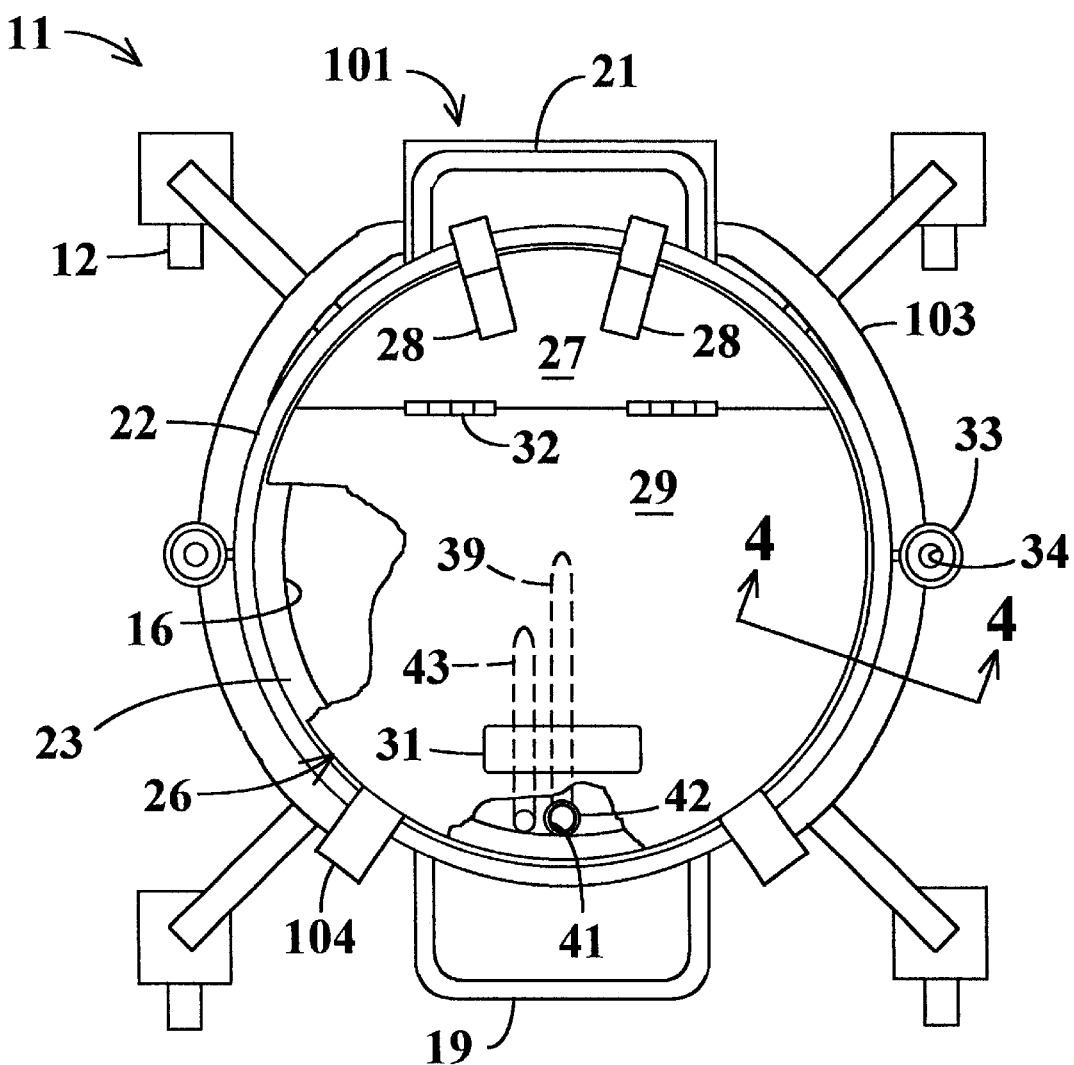
FIG. 3 is a top view of the sterilizer and waste collection cart of the preceding figures.

Referring initially to FIGS. 1, 2 and 3 of the drawings, a sealable pressure resistant sterilizer vessel is provided with ground wheels 12 which enable the sterilizer vessel to also be used as a portable waste collection cart 11. The combined sterilizer vessel and collection cart 11 eliminates any need for transferring untreated infectious wastes from a collection cart to a sterilizer vessel.

Figure 4:
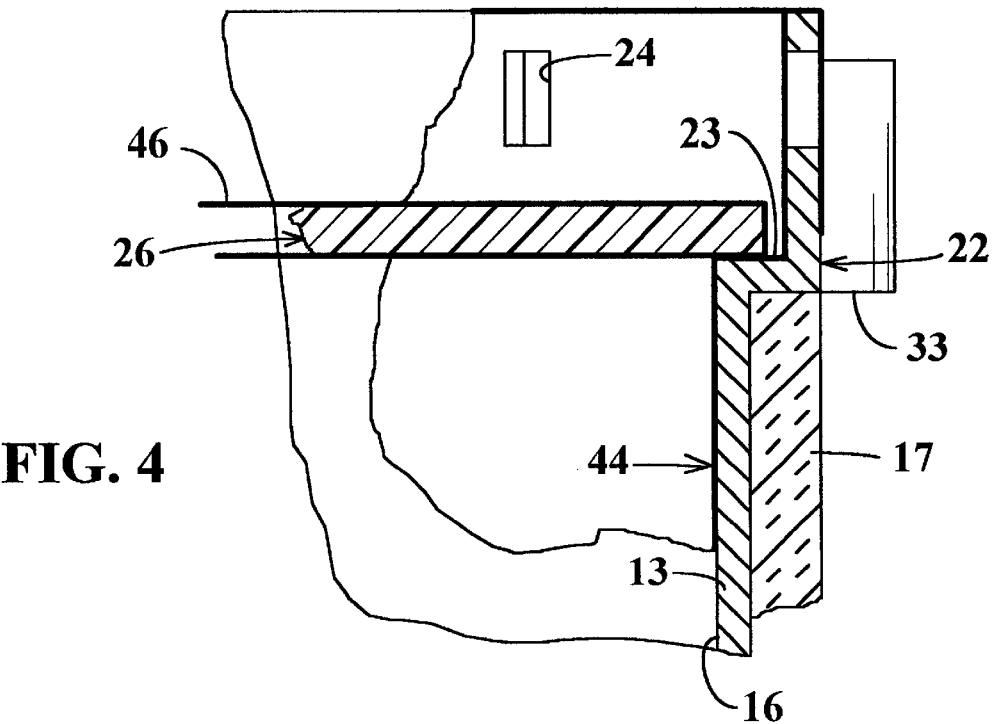
FIG. 4 is a section view taken along line 4—4 of FIG. 3.

With reference jointly to FIGS. 1, 3 and 4, the sterilizer vessel and collection cart 11 of this example includes a pressure resistant metal drum 13 with an opening 14 at the top and which forms a chamber 16 in which wastes are deposited and later sterilized. An outer shell 17 of thermal insulation encases the drum 13 except at the opening 14. The wheels 12 which support the sterilizer vessel and collection cart 11 are attached to the base of the cart by brackets 18 and are preferably of the swiveling type. A U-shaped push handle 19 extends outward from the back of the cart 11 preferably at an elevation corresponding approximately to the waist level of an adult person of average size. Two vertically spaced U-shaped lifting handles 21 extend outward at the front of the cart 11 to enable lifting and tilting of the cart by dumping mechanism as will hereinafter be described.

An annular flange 22 of angled cross section at the top of drum 13 enables sealing of the chamber 16 during the sterilization step. The flange 22 forms an annular step 23, encircling the chamber opening 14, against which a seal can be compressed. The flange 22 is penetrated by angularly spaced apart apertures 24 for purposes to be hereinafter described.

The cart 11 is provided with a removable circular lid 26 which is seated against step 23 within flange 22 during periods when the cart is being used for waste collection and storage at the source of the wastes. Lid 26 has a first section 27 which is held in place by a pair of clips 28 which extend upward and outward from the first section and which may be integral portions of the lid section 27 provided that it is formed of slightly resilient material. Clips 28 are shaped and positioned to snap engage in the pair of flange apertures 24 which are closest to the front of the cart 11.

The removable lid 26 has a second larger section 29, provided with an upward extending handle 31, which is hinged to the first section 27 by a pair of hinges 32. Thus the chamber 16 may be opened for deposit of wastes therein by grasping handle 31 and pivoting the second lid section 29 upward.

Further components of the cart 11 include a pair of closure positioning pin guides 33 which are secured to flange 22 at diametrically opposite locations therearound. Each such guide 33 has a tapered vertically extending passage 34 which is of progressively diminishing diameter in the downward direction. The guides 33 serve to assure correct registry of the cart 11 with a sealing closure during the sterilization stage of operation in a manner which will be hereinafter described.

Figure 5:
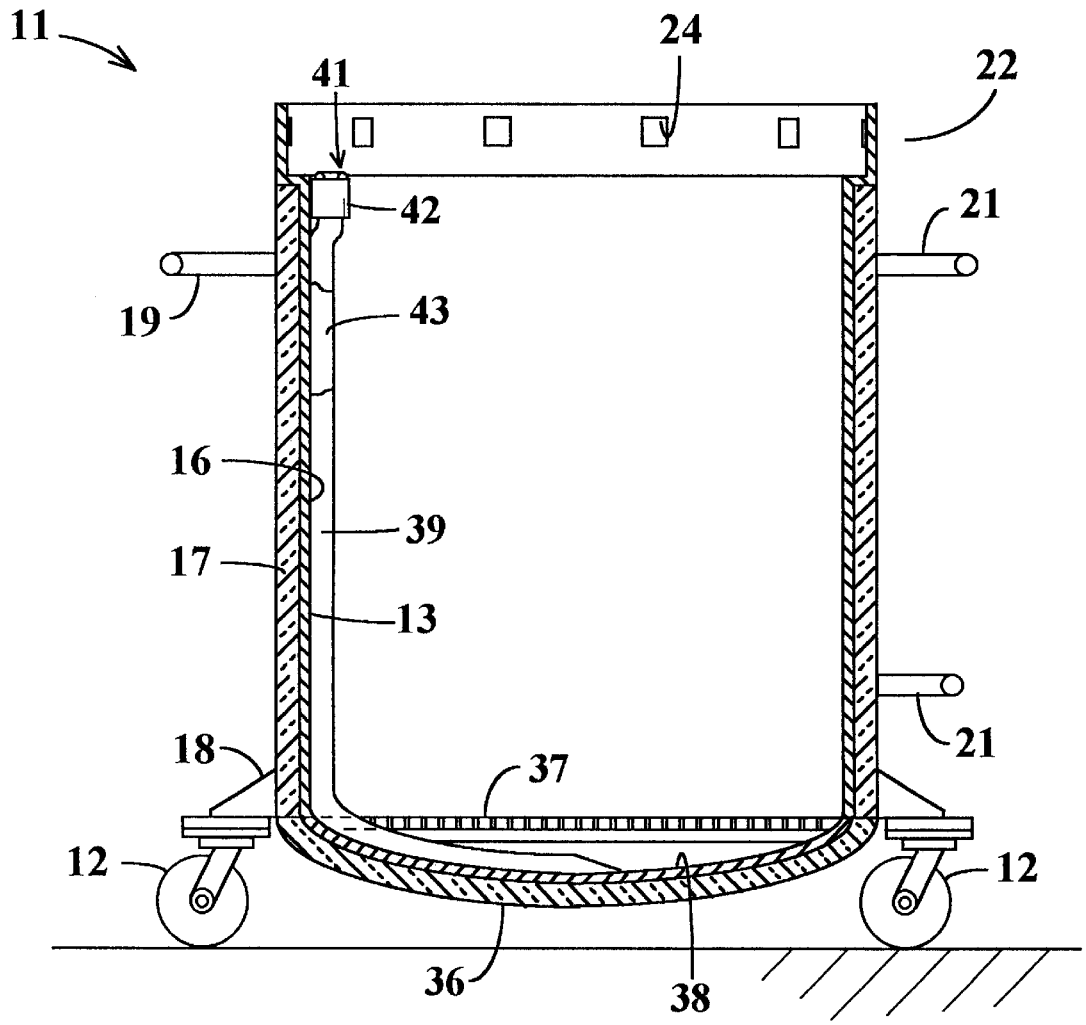
FIG. 5 is an elevation section view of the sterilizer and waste collection cart of the preceding figures.

Referring to FIGS. 3 and 5, the base 36 of the drum 13 and outer shell 17 has an inverted dome shape and a horizontally oriented perforated circular plate 37 extends across the lowermost region of chamber 16 within the base. This forms a steam condense collection sump 38 at the bottom of the chamber. A condensate extraction tube 39 extends upward, along the inside surface of drum 13, from the center of the bottom of sump 38 to the level of the previously described step 23 that is formed by the drum flange 22. A circular resilient seal 41 seats in an enlargement 42 at the top of the extraction tube 39 and provides for connection to a condensate pump in a manner which will be hereinafter described. A second tube 43 extends upward along the inside surface of drum 13 from the sump 38 to a location which is slightly below the step 23. During the sterilization step, tube 43 assures that steam directed into the top region of chamber 16 is not blocked from the bottom region by material contained within the chamber. The tube 43 also assures equalization of pressure at the top and bottom regions of the chamber 16 during the sterilization step.

Referring jointly to FIGS. 1 and 4, the drum 13 is provided with a disposable liner 44 prior to deposit of wastes in the cart 11. The liner 44 may be a bag formed of thin flexible plastic and extends over the drum flange 22 and downward for a distance along the outer surface of the flange. The liner 44 is formed of one of the heat resistant plastics, such as polypropylene for example, which remains intact at the high temperatures to which the contents of the cart 11 are subjected during the sterilization step. This protects the inner surface of drum 13 from fouling by other plastics or substances in the waste that melt at the high temperature and which might adhere to the drum wall in the absence of the liner 44. Referring jointly to FIGS. 3 and 4, a disposable cover 46 encases the lid 26 during the waste collection step to prevent contamination of the lid. Cover 46 is also formed of flexible plastic. Lid 26 is detached from the cart 11 just prior to the sterilization step and the disposable lid cover 46 is added to the collected wastes within the cart 11.

Figure 6:
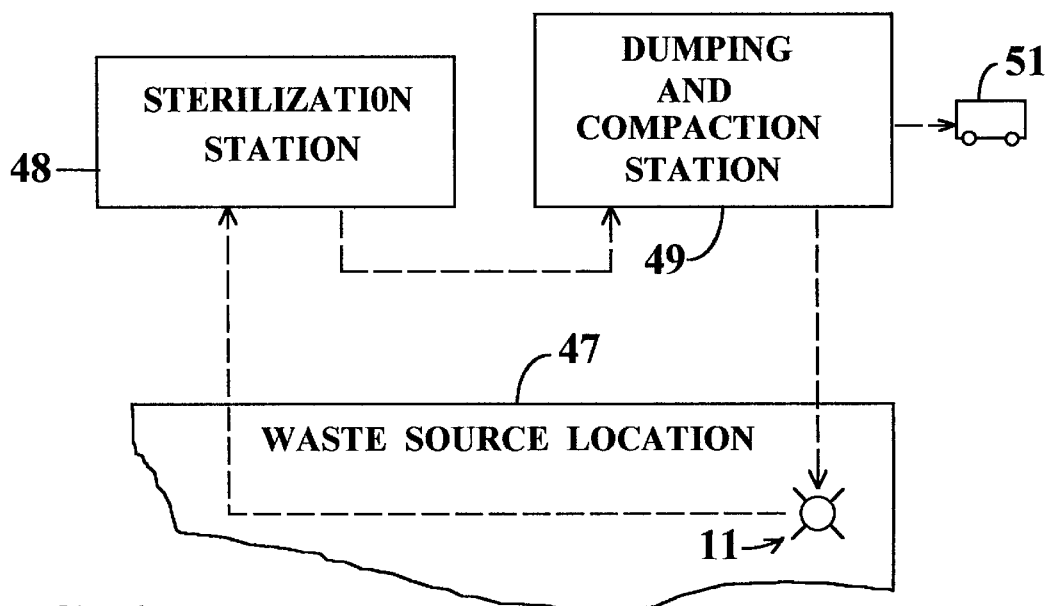
FIG. 6 is a block diagram depicting a typical route of travel of the sterilizer and waste collection cart during usage thereof.

In a typical usage of the portable sterilizer vessel and collection cart 11, with reference to FIG. 6, the cart is initially situated at or close to a location at which infectious wastes originate. The source location 47 may typically be within a hospital, medical clinic or the like although there are other types of facilities at which such wastes may be produced. A number of the sterilizer vessel and collection carts 11 may be stationed within large facilities where infectious wastes are produced at a number of different locations.

When a cart 11 has been filled with wastes it is manually pushed or pulled to a sterilization station 48 where steam sterilization of the contents is effected prior to emptying of the cart. The cart 11 still containing its original contents is then pushed or pulled to a dumping and compaction station 49 where the sterilized contents of the cart are loaded into transportable bins 51 which may be hauled to a landfill or other disposal site.

In one mode of operation, this waste collection and sterilization procedure eliminates any need to transfer infectious wastes from one receptacle to another after the initial depositing of the wastes in a collection receptacle. In another mode of operation, the wastes may be initially deposited in conventional plastic bag lined collection receptacles. The combined sterilizer vessel and collection cart 11 may then be used to collect filled bags from a number of such receptacles. While this requires a transfer of filled bags from one receptacle to another, it is still advantageous as only a single such transfer is needed. An additional transfer of the infectious wastes into a sterilizer vessel is not needed as in the conventional practice.

The process has advantages additional to that of reducing handling of untreated wastes. Greater flexibility in the location of components of a waste processing system is made possible. For example, portability of the waste sterilizing vessel allows the dumping and compaction components to be located away from the sterilizing station in instances where that is desirable because of space limitations or for other reasons. The waste processing system as a whole can be more compact as the functions of a collection cart and a waste sterilizer vessel are combined into one unit.

Figure 8:
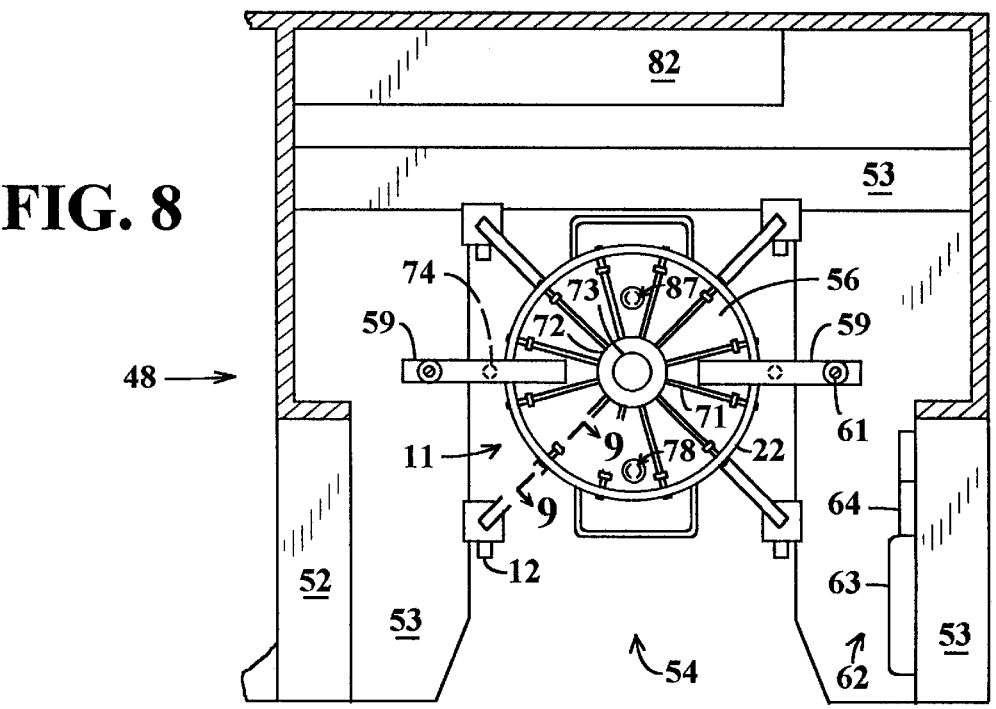
FIG. 8 is a plan section view of portion of the sterilizing station taken along line 8—8 of FIG. 7.
Figure 7:
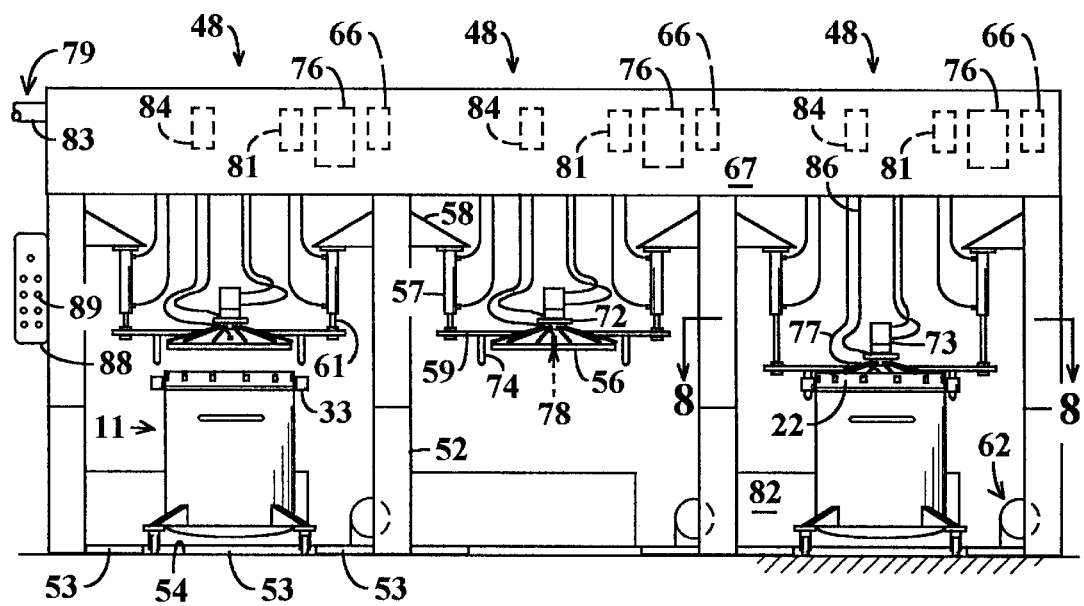
FIG. 7 is a frontal view of a sterilizing station at which the contents of sterilizer and waste collection carts are sterilized.

Referring to FIGS. 7 and 8 in conjunction, this example of the invention utilizes three sterilization stations 48 to enable simultaneous processing of more than one cart. A single sterilization station 48 or a larger number of sterilization stations may be appropriate depending on the amount of waste which needs to be processed at the particular facility.

The sterilization stations 48 of this example are disposed in side-by-side relationship within framing 52. Linear frame members 53 extend along the floor or pavement which underlies each station 48 to define a rectangular cart parking site 54. Frame members 53 are positioned to locate the cart 11 directly below a sealing closure 56 which replaces the previously described lid of the cart and which seals the sterilization chamber of the cart during the sterilization step.

The sealing closure 56 of this example is supported by a pair of vertically oriented linear hydraulic actuators 57 which extend downward at opposite sides of the cart 11 from brackets 58 attached to framing 42. Support arms 59 extend laterally from opposite sides of the top of closure 56 and are secured to the lower ends of the extendible and retractable rods 61 of the hydraulic actuators 57. Thus extension of the actuator rods 61 lowers the closure 56 into the flange 22 at the top of the cart 11 and retraction of the rods raises the closure out of the cart. Pressurized hydraulic fluid for operating the actuators 57 is provided by a hydraulic fluid supply 62 situated at the base of the sterilization station 48 at one side of the cart parking site 54. The hydraulic fluid supply 62 includes a fluid reservoir 63 and motor driven pump 64 which may be of conventional design. A solenoid controlled valve 66 for selectively supplying hydraulic fluid to opposite ends of the actuators 57 is situated within an overhead portion 67 of the station framing 52.

Figure 9:
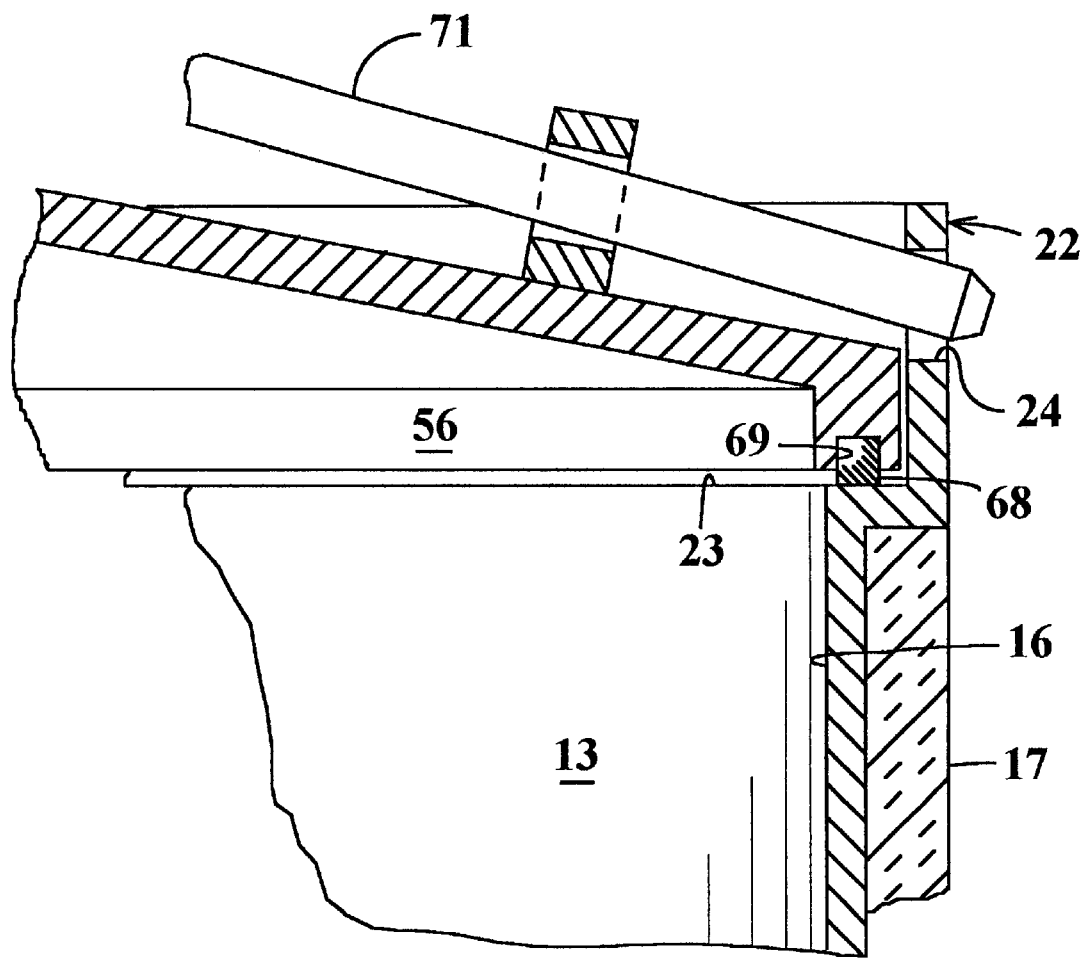
FIG. 9 is a section view taken along line 9—9 of FIG. 8.

Referring jointly to FIGS. 8 and 9, an annular heat resistant resilient seal 68 is disposed within an annular groove 69 at the underside of the peripheral region of closure 56. The seal 68 protrudes downward from the closure 56 and is proportioned and positioned to seat against the previously described step 23 formed by the flange 22 at the top of the cart 11. Thus downward pressure on the closure 56 compresses the seal. 68 and hermetically seals the sterilization chamber 16. The downward pressure can be exerted by the previously described fluid actuators but the resulting force is exerted on the entire cart including the support wheels and may unevenly compress different portions of the seal 68. It is preferable that the closure 56 be of the known form having radially directed crimp arms 71 which extend and pivot in response to turning of a control wheel 72 in a manner which causes the arms to enter the apertures 24 in flange 22 and to crimp the closure and flange together. The detailed construction of such closures, used for such purposes as sealing bulkhead openings in ships, is known to the art.

The control wheel 72 may be turned manually if desired but in this example is turned by a reversible electrical motor 73 carried by the closure 56. Alternately, motor 73 may be a hydraulic motor.

One of pair of vertically directed positioning pins 74 extends downward from each of the closure support arms 59. Referring to FIGS. 3 and 7 in conjunction, pins 74 are positioned to enter the previously described pin guides 33 at each side of the cart 11 and act to assure that the step 23 at the chamber opening is in precise register with the closure 56 in order to effect the sealing operation. As the guide passages 34 in the guides 33 are tapered, downward travel of the pins 74 can shift the cart 11 laterally if necessary to assure registry.

Air is evacuated from the sealed sterilization chamber 16 at the start of a sterilization step and high temperature pressurized steam is directed into the chamber for a period of time sufficient to destroy infectious organisms. Steam condensate is evacuated from the chamber during this period. The initial evacuation of air is desirable as pockets of air within plastic bags and the waste itself constitute thermal insulation which can slow the transfer of heat to the wastes.

Referring to FIGS. 5 and 7, the evacuation pump 76 of this example is situated in the overhead portion 67 of framing 52 and is coupled to the sterilization chamber 16 through a flexible hose 77 which connects with the closure 56 and which has sufficient slack to accommodate to the vertical movement of the closure. Hose 77 communicates with a passage 78 in closure 56 located to seat over the previously described enlargement 42 and seal 41 at the top of extraction tube 39. Pump 76 is preferably of the known steam jet operated aspirator type and receives steam from the steam supply 79 through solenoid operated control valve 81. Steam condensate extracted from the sterilization chamber 16 is temporarily stored in a condensate tank 82 at the back of the sterilization station.

Many hospitals and the like have a pre-existing source of steam which is used for heating and/or other purposes. The steam supply 79 of this sterilization station 48 is simply a conduit 83 which is connectable to a pre-existing steam source. A boiler for generating steam can be provided in instances where a pre-existing steam source is not available. Steam from the supply 79 is directed into the sterilzation chamber 16 through a solenoid operated control valve 84 and another flexible tube 86 which connects with a passage 87 in closure 56.

A housing 88 at one side of the sterilization station framing 52 contains switches 89 for selectively energizing and operating the electrically controlled devices such as solenoid operated valves 66, 81 and 84, closure motor 73 and the motor driven hydraulic fluid pump 84. Automatic cycling of these devices can be provided for if desired.

Figure 10:
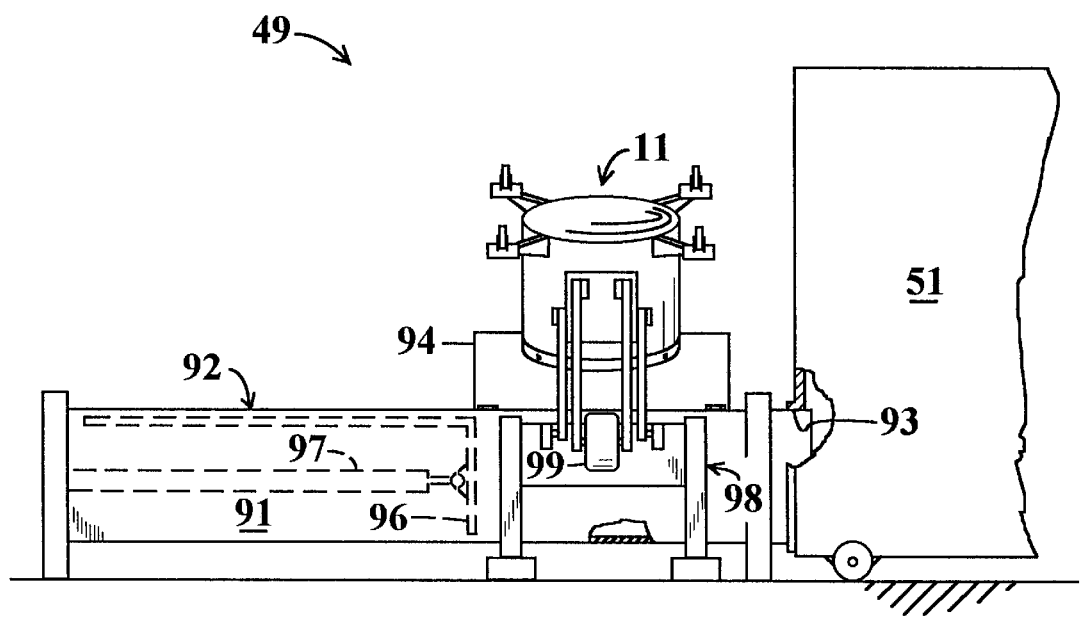
FIG. 10 is an elevation view of a dumping and compaction station at which the sterilized contents of the sterilizer and waste collection carts are transferred to transportable bins for disposal.

Referring to FIG. 10, the dumping and compaction station 49 has a compactor 91 which may of the known type in which a elongated housing 92 extends a short distance into a conforming opening 93 at the base of a transportable bin 51 which can be loaded onto a truck and hauled to a landfill or the like for disposal of wastes. Wastes deposited through a door 94 at the top of the compactor housing 92 are forced into the bin 51 and compacted in the process by a translatable ram plate 96 within the housing that is driven by extendible hydraulic actuators 97. The station 49 also includes a dumper 98 which may be of one of the known types. The dumper 98, operated by a rotary hydraulic actuator 99 in this example, engages the lifting handles 21 of cart 11 and lifts and tilts the cart to deposit the contents in compactor 91. The cart 11 is then returned to the source of the infectious wastes for reuse in the manner which has been previously described.

Referring again to FIGS. 1, 2 and 3, a detachable air evacuation unit 101 can protect personnel from airborne contamination during the initial deposit of wastes in the cart 11. The unit 101 of this example has a casing 102 shaped to rest against the exterior side surface of cart 11. Casing 102 is suspended from the drum flange 22 by two air intake tubes 103 which have air intake fittings 104 at their upper ends that are also clips that fit onto the top of the flange 22. Air intake openings 106 in the fittings 104 face the region that is immediately above the waste receiving chamber 16.

Casing 102 contains an air filter 107 preferably of the dual process HEPA type which is disposed against a slotted outer wall 108 of the casing that allows air which has been directed through the filter to escape from the casing. An air pump 109 within casing 102 draws air into intake fittings 104 through tubes 103 and discharges the air through filter 107. Pump 109 is driven by an electrical motor 111 in casing 102 that is energized by a rechargeable battery 112. A control switch 113 on casing 102 enables a person who is about to deposit wastes in the cart 11 to turn the motor 111 on prior to opening the lid 29 of the cart 11. Consequently, air flow from the opened chamber 16 is drawn into fittings 104 and is filtered rather than traveling towards the person who is depositing waste. The air evacuation unit 101 preferably includes a timer 114, which may be adjustable, that automatically shuts motor 111 off after a period of time sufficient to accomplish the deposit of wastes. The air evacuation unit 101 may be detached from cart 11 during sterilization step.

Figure 11:
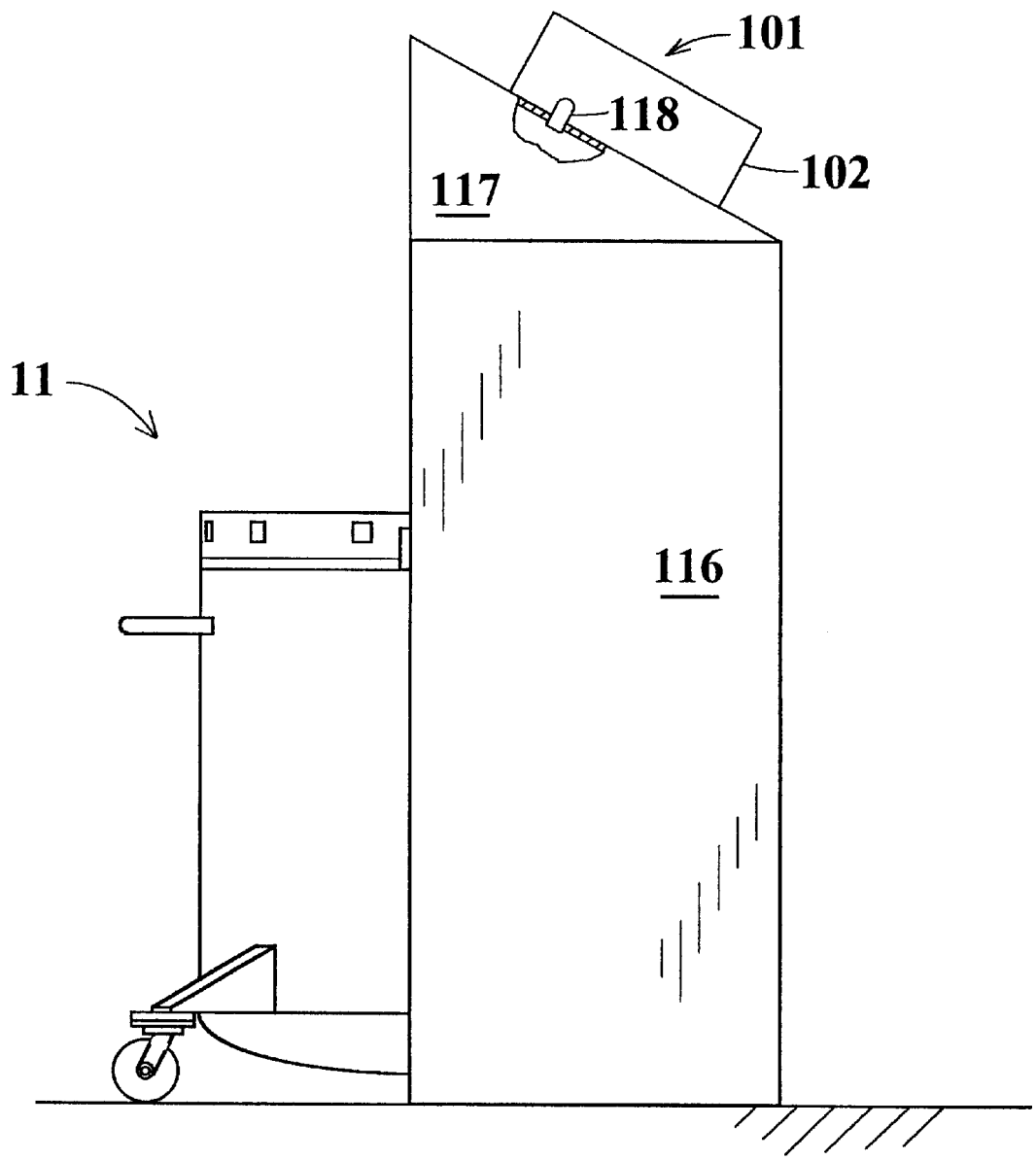
FIG. 11 is a side view of an air evacuation system for protecting persons who deposit wastes in the cart from airborne contamination.

The direct attachment of the air evacuation unit 101 to the cart 11 for travel therewith is particularly advantageous when the cart is used as a collection cart to pick up wastes which have been initially deposited in a series of receptacles situated at different locations. Referring now to FIG. 11, a different arrangement of the unit 102 can be advantageous where the cart 11 remains at one location during the waste collection step and is itself the receptacle into which wastes are initially deposited. In this mode of operation, the cart 11 may be partially entered into an open fronted fixed housing 116 which has a hood 117 at the top that partially encloses the region above the cart 11. An air evacuation unit 101, essentially similar to that previously described, is secured to the back of the hood 117. The relatively long air intake tubes of the previously described embodiment may be replaced with shorter tubes 118 which draw air through the hood from the region which is above cart 11 during periods when the cart is opened for deposit of wastes.

While the invention has been described with reference to certain specific embodiments for purposes of example, many modifications and variations are possible and it is not intended to limit the invention except as defined in the following claims.

What is claimed is:

1. Biohazardous waste processing apparatus having a waste sterilizer vessel forming a chamber with an opening for receiving the wastes which opening is hermetically sealable by disposition of a sealing closure thereat to enable sterilization of the contents of the vessel by admission of steam into the chamber, wherein the improvement comprises:

said waste sterilizer vessel also being a portable waste collection cart which rides on support wheels enabling travel of the vessel between a first location at which said waste is collected and a second location at which said sterilization is performed, said sealing closure is a component of a sterilization station at said second location and is raisable and lowerable above a portable waste collection and sterilizer vessel cart parking site thereat.

2. The apparatus of claim 1 further including a waste compactor and a vessel dumper situated at a third location, said dumper being positioned to lift and tilt said portable waste collection and sterilizer vessel cart to dump the contents thereof into said waste compactor.

3. The apparatus of claim 1 further including a lid seatable at said chamber opening at said first location, said lid being removable from said opening to enable seating of said sealing closure thereat at said second location.

4. The apparatus of claim 1 wherein said portable waste collection and sterilizer vessel cart has at least a pair of positioning pin guides secured thereto and which have laterally spaced apart vertical passages and wherein said sealing closure is a raisable and lowerable component of a sterilization station at said second location and is situated above a portable waste collection and sterilizer vessel cart parking site thereat, further including at least a pair of vertical positioning pins which are joined to said sealing closure, said positioning pins being located to extend into said vertical passages of said positioning guides when said sealing closure is in register with said chamber opening.

5. The apparatus of claim 4 wherein upper regions of said vertical passages of said positioning guides have diameters that are greater than the diameters of said positioning pins and wherein the diameters of said passages progressively diminish in the downward direction, lower regions of said passages having diameters conforming substantially to the diameters of said positioning pins whereby downward motion of said positioning pins in said passages laterally shifts said waste collection and sterilizer vessel cart if necessary to bring said chamber opening into register with said sealing closure.

6. The apparatus of claim 1 wherein said portable waste collection and sterilizer vessel cart has a flange forming an annular step which encircles said chamber opening and wherein said sealing closure carries an annular compressible seal proportioned and positioned to seat against said step, and wherein said sealing closure is a component of a sterilization station at said second location and is raisable and lowerable above a portable waste collection and sterilizer vessel cart parking site thereat, said sterilization station further including means for crimping said sealing closure and said flange together to compress said seal.

7. The apparatus of claim 1 further including a sterilization station at said second location forming a stall at which said portable waste collection and sterilizer vessel cart may be temporarily parked, said sealing closure being a component of said sterilization station and being movable into engagement which said chamber opening to close said opening, said sealing closure having first and second passages which extend therethrough, a steam supply communicated with said first passage through a steam conduit and a condensate pump communicated with said second passage through a condensate conduit.

8. The apparatus of claim 7 wherein said portable waste collection and sterilizer vessel cart has a perforated plate extending across said chamber at a bottom region of said chamber forming a condensate collection sump thereat, further including a condensate withdrawal tube extending upward within said chamber of said portable waste collection and sterilizer vessel cart from said sump to a location at which said condensate withdrawal tube communicates with said second passage of said sealing closure when said sealing closure is seated at said chamber opening.

9. The apparatus of claim 8 wherein said portable waste collection and sterilizer vessel cart further includes a pressure equalization conduit extending vertically within said chamber between said condensate collection sump and the uppermost region of said chamber.

10. The apparatus of claim 7 wherein a plurality of said sterilization stations are situated at said second location enabling simultaneous processing of the contents of a plurality of said portable waste collection and sterilizer vessel carts.

11. The apparatus of claim 1 further including a filter and a motor driven air pump having at least one air intake positioned to draw air from a region which is above said chamber and having an outlet which discharges said air through said filter.

12. The apparatus of claim 11 wherein said filter and air pump and a drive motor therefor are contained within a detachable casing which is fastened to said portable waste collection and sterilizer vessel cart and which is movable therewith.

13. The apparatus of claim 12 including a pair of said air intakes, said air intakes including a pair of air tubes which extend from said casing to clips which engage a rim portion of said cart and which suspend said casing therefrom.

14. The apparatus of claim 11 further including a housing situated at said first location, said housing having a hood under which said portable waste collection and sterilizer vessel cart extends when said cart is parked at said first location to receive wastes, said filter and air pump and air intake being secured to said hood.

15. The apparatus of claim 11 further including a manually operable switch at said housing for initiating operation of said motor driven air pump, and a timer for terminating said operation of said motor driven air pump after a period of time.

16. The apparatus of claim 1 wherein said portable waste collection and sterilizer vessel cart has a flange encircling said chamber opening and forming an annular step which encircles said chamber opening, said flange having a plurality of closure engaging apertures situated at angular intervals around said flange, and wherein said sealing closure has a plurality of crimping arms which are movable into said closure engaging apertures to press said sealing closure against said step.

17. The apparatus of claim 16 further including a lid seatable against said step after withdrawal of said sealing closure therefrom, said lid having a pivoting portion hinged to a non-pivoting portion which is secured in place by resilient clips which snap engage in ones of said closure engaging apertures.

18. Biohazardous waste collection and processing apparatus comprising:

a portable sealable waste collection vessel formed of pressure resistant and thermally insulative material and having an opening through which biohazardous waste is deposited in said vessel, said waste collection vessel being supported on wheels which enable travel of said vessel between a first location at which said waste originates and a second location at which the wastes within said vessel are sterilized by direction of steam into said vessel, an openable lid for closing said opening at said first location, said lid being temporarily replaceable by a sealing closure at said second location which sealing closure seals said vessel during direction of steam into said vessel.

19. In a method for processing biohazardous wastes which originate at a first location and which are sterilized at a second location, the steps comprising:

utilizing a wheeled sealable pressure resistant sterilizer vessel at said first location for receiving said wastes at first location, wheeling said wheeled sealable sterilizer vessel to said second location, (temporarily sealing said wheeled sealable sterilizer vessel at said second location while said wastes remain therein,)

utilizing an openable lid to close said wheeled sealable sterilizer vessel at said first location, and temporarily replacing said openable lid with a sealing closure at said second location during sterilization of said wastes thereat, and sterilizing said wastes at said second location by injecting steam into the wheeled sealable sterilizer vessel prior to removal of said wastes from said vessel.

20. The method of claim 19 including the further steps of traveling said wheeled sealable sterilizer vessel to a waste compactor at a third location following sterilization of said wastes and prior to removal of the wastes therefrom, and transferring the sterilized wastes from said wheeled sealable sterilizer vessel to said compactor at said third location.

21. The method of claim 19 including the further step of returning said wheeled sealable sterilizer vessel to said first location for further receipt of wastes thereat.

22. The method of claim 19 including the further steps of withdrawing an air flow from said wheeled sealable sterilizer vessel at said first location while said vessel is opened to deposit wastes therein, and filtering the air flow prior to discharge thereof.

* * * * *